United States Patent [19]
Zeeman

[11] Patent Number: 5,865,797
[45] Date of Patent: Feb. 2, 1999

[54] FLUID DELIVER SYSTEM

[76] Inventor: Mary L. Zeeman, P.O. Box 260, Jenkintown, Pa. 19046

[21] Appl. No.: 792,945

[22] Filed: Jan. 21, 1997

[51] Int. Cl.[6] ....................................................... A61M 5/14
[52] U.S. Cl. ............................. 604/80; 604/246; 604/249; 604/250
[58] Field of Search ................................ 604/80, 82, 83, 604/85, 86, 81, 246, 249, 250, 258, 257, 262, 403; 222/145

[56] References Cited

U.S. PATENT DOCUMENTS

| | | | |
|---|---|---|---|
| 3,411,534 | 11/1968 | Rose | 604/250 |
| 4,673,389 | 6/1987 | Archibald et al. | 604/81 |
| 4,869,721 | 9/1989 | Karpisek | 604/250 |

*Primary Examiner*—Wynn Wood Coggins
*Assistant Examiner*—N. Kent Gring

[57] ABSTRACT

A fluid deliver system including a pair of bags having an opening formed in a bottom edge thereof. The bags include a first bag for containing a first liquid and a second bag for containing a second liquid. Further provided is a pair of elongated lumens each with a top open end and a bottom open end. Each top open end of the lumens is connected in communication with the openings of a corresponding bag. The bottom ends are in communication with each other to form an exit conduit and communicable with a dispensable apparatus for inserting into an arm of a patient. Finally, a drip control means is provided with a roller for manually controlling the amount of the first fluid and second fluid which exits the lumens and enters a patient.

7 Claims, 3 Drawing Sheets

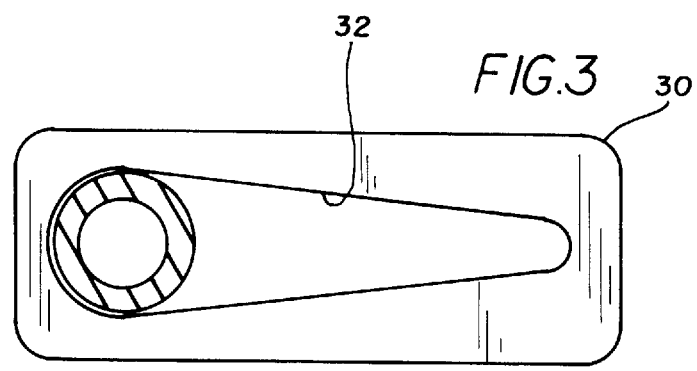
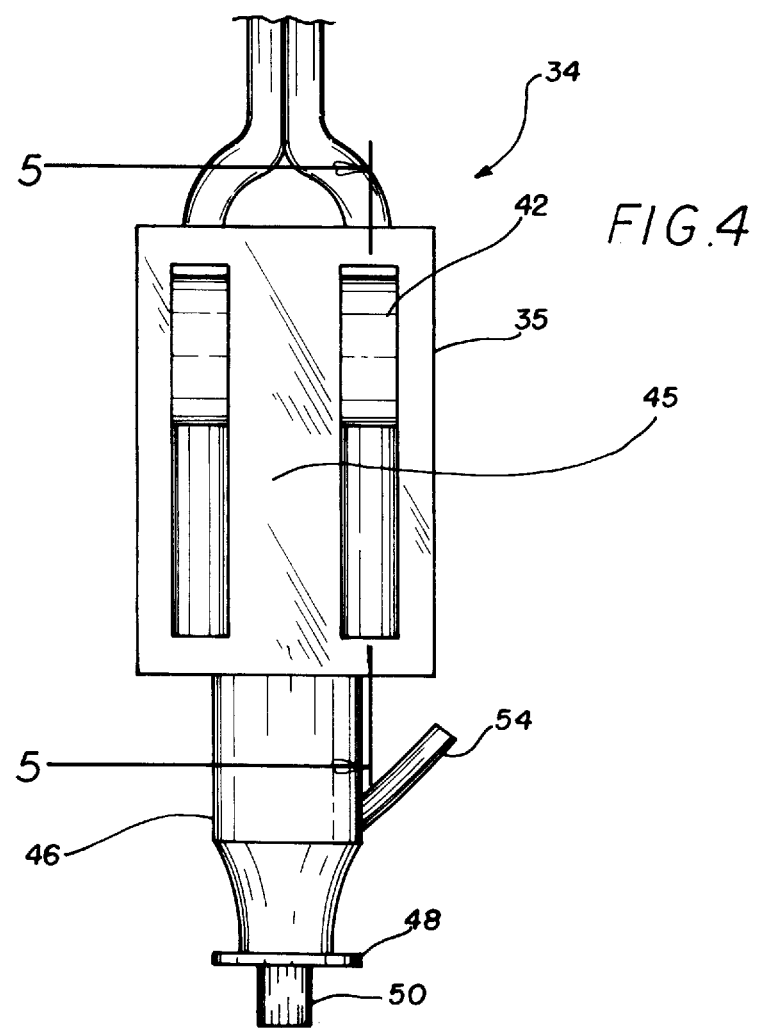

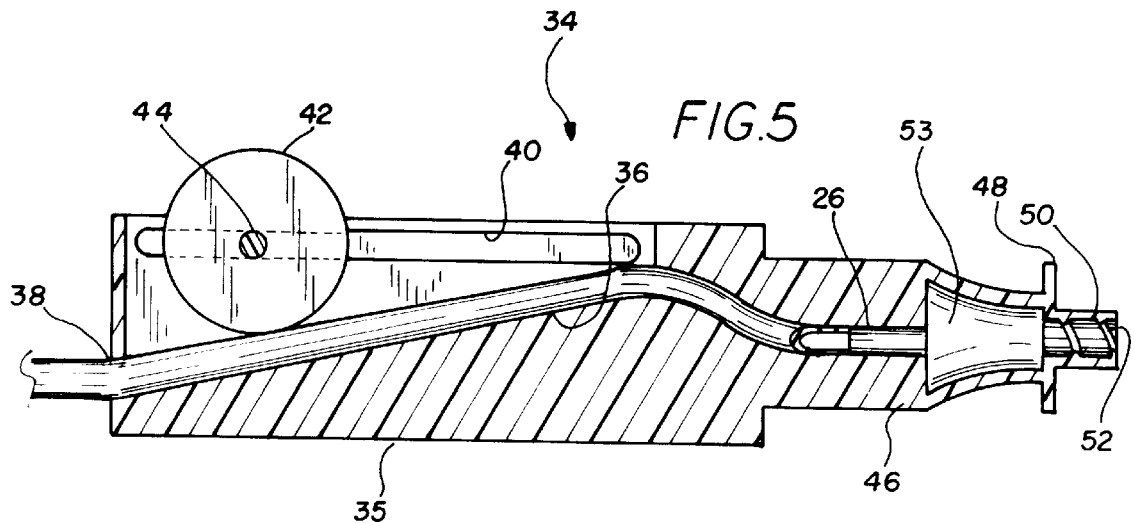
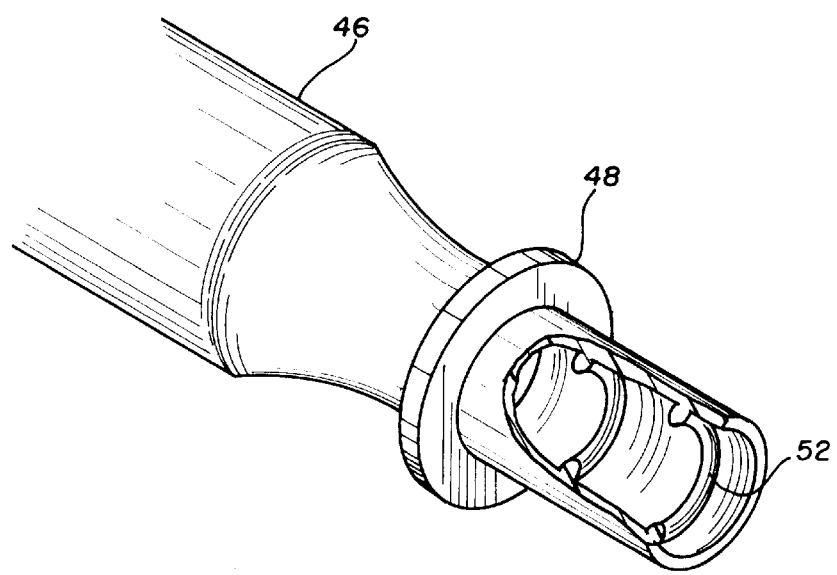

FLUID DELIVER SYSTEM

BACKGROUND OF THE INVENTION

1. Field of the Invention

The present invention relates to a fluid deliver system and more particularly pertains to controlling the rate and mixture of fluid administered to a patient.

2. Description of the Prior Art

The use of fluid dispensing devices is known in the prior art. More specifically, fluid dispensing devices heretofore devised and utilized for the purpose of administering fluid to a patient are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 4,257,416 to Prager; U.S. Pat. No. 4,512,764 to Wunsch; U.S. Pat. No. 5,431,185 to Shannon et al.; U.S. Pat. No. 5,207,642 to Orkin et al.; U.S. Pat. No. 4,559,036 to Wunsch; and U.S. Pat. No. Des. 278,181 to Archibald et al.

In this respect, the fluid deliver system according to the present invention substantially departs from the conventional concepts and designs of the prior art, and in so doing provides an apparatus primarily developed for the purpose of controlling the rate and mixture of fluid administered to a patient.

Therefore, it can be appreciated that there exists a continuing need for a new and improved fluid deliver system which can be used for controlling the rate and mixture of fluid administered to a patient. In this regard, the present invention substantially fulfills this need.

SUMMARY OF THE INVENTION

In view of the foregoing disadvantages inherent in the known types of fluid dispensing devices now present in the prior art, the present invention provides an improved fluid deliver system. As such, the general purpose of the present invention, which will be described subsequently in greater detail, is to provide a new and improved fluid deliver system which has all the advantages of the prior art and none of the disadvantages.

To attain this, the present invention essentially comprises a pair of bags each constructed from a formidable material. Each bag has an eyelet formed on a top edge thereof for allowing the coupling thereof to a horizontally oriented support. Such coupling is afforded preferably via a ring. An opening is formed in a bottom edge of each of the bags. The bags include a first bag for containing a first liquid and a second bag for containing a second liquid. As shown in FIG. 1, a pair of elongated lumens are provided each with a top open end and a bottom open end. The lumens consist of a first lumen with a first diameter and a second lumen with a second diameter which is larger than the first diameter. See FIG. 2. The bottom open end of each lumen is fused together to form a single exit conduit. It should be noted that the lumens are connected in parallel relationship along lower halves thereof. Further included is a pair of filters each connected between the opening of a corresponding bag and the top open end of a corresponding lumen. Such filters are included for filtering the fluid which flows therethrough to the lumens. As best shown in FIGS. 1 & 3, a pair of cinches are included. Such cinches are situated on each of the lumens adjacent the top open ends thereof. Each cinch is formed of a small rectangular plate with a generally triangular shaped cut out formed therein. Note FIG. 3. As such, a lumen may be situated within each cut out such that the plate may be slid laterally to selectively preclude the flow of fluid therethrough. With specific reference to FIGS. 4-6, a drip control assembly includes a rear extent with a rectangular configuration having a bottom face, a rear face, a front face, and a pair of side faces defining an open top face and an interior space. The interior space is defined by a bottom incline and a pair of vertical side walls. The rear wall has an aperture situated adjacent the bottom face for allowing the passage of the lumens therethrough such that the lumens reside along the bottom incline of the interior space. As shown in FIG. 5, the side walls of the assembly have a pair of horizontally situated grooves formed therein along the top face. The drip control assembly further includes a cylindrical roller with a pair of pins integrally formed coaxially on end faces thereof. Such pins are adapted for being slidably situated within the grooves such that the outflow of the fluid from the exit conduit of the lumens may be controlled. The drip control assembly further has a front extent with a cylindrical configuration. Such front extent includes a first end integrally formed with the front face of the rear extent. The bottom open end of the of the lumens is situated coincident with a second end of the front extent of the drip control assembly. The front extent further has an annular flange formed coincidently with the second end thereof. See FIG. 6. An adapter tube is integrally coupled to the second end in communication with the exit conduit of the lumens for allowing fluid to pass therethrough. It should be noted that the adapter tube has a threaded detent formed therein for allowing the attachment of dispensing mechanisms thereto. Finally, an emergency tube is provided with a first end situated within the front extent of the drip control assembly in communication with the lumens.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved fluid deliver system which has all the advantages of the prior art fluid dispensing devices and none of the disadvantages.

It is another object of the present invention to provide a new and improved fluid deliver system which may be easily and efficiently manufactured and marketed.

It is a further object of the present invention to provide a new and improved fluid deliver system which is of a durable and reliable construction.

An even further object of the present invention is to provide a new and improved fluid deliver system which is susceptible of a low cost of manufacture with regard to both materials and labor, and which accordingly is then susceptible of low prices of sale to the consuming public, thereby making such fluid deliver system economically available to the buying public.

Still yet another object of the present invention is to provide a new and improved fluid deliver system which provides in the apparatuses and methods of the prior art some of the advantages thereof, while simultaneously overcoming some of the disadvantages normally associated therewith.

Still another object of the present invention is to control the rate and mixture of fluid administered to a patient.

Lastly, it is an object of the present invention to provide a new and improved fluid deliver system including a pair of bags having an opening formed in a bottom edge thereof. The bags include a first bag for containing a first liquid and a second bag for containing a second liquid. Further provided is a pair of elongated lumens each with a top open end and a bottom open end. Each top open end of the lumens is connected in communication with the openings of a corresponding bag. The bottom ends are in communication with each other to form an exit conduit and communicable with a dispensable apparatus for inserting into an arm of a patient. Finally, a drip control means is provided with a roller for manually controlling the amount of the first fluid and second fluid which exits the lumens and enters a patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of one of the cinches taken along line 3—3 shown in FIG. 1.

FIG. 4 is a top view of the drip control assembly.

FIG. 5 is a cross-sectional view of the drip control assembly taken along line 5—5 shown in FIG. 4.

FIG. 6 is a perspective view of the front extent of the drip control assembly.

Similar reference characters refer to similar parts throughout the several views of the drawings.

DESCRIPTION OF THE PREFERRED EMBODIMENT

Figure 1:
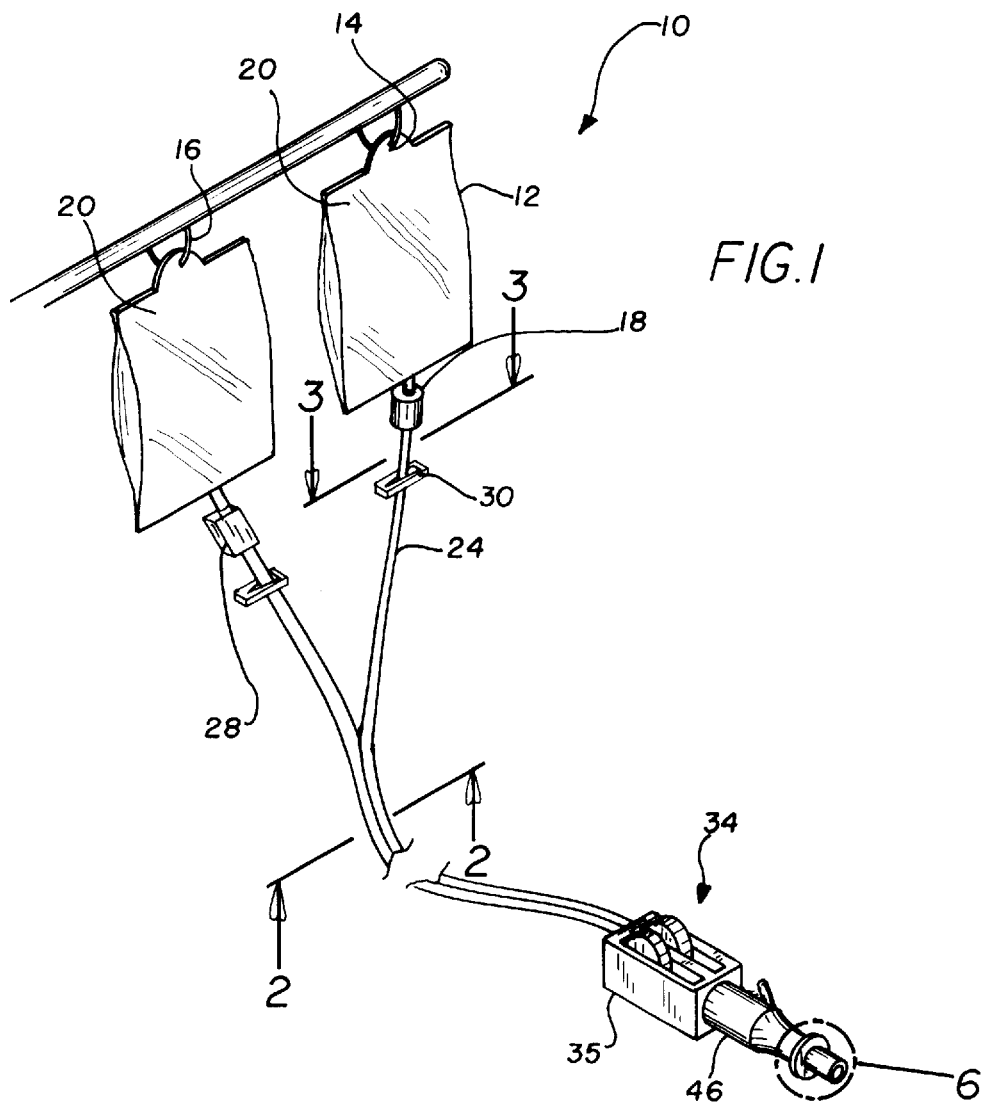
FIG. 1 is a perspective illustration of the preferred embodiment of the fluid deliver system constructed in accordance with the principles of the present invention.

With reference now to the drawings, and in particular to FIG. 1 thereof, a new and improved fluid deliver system embodying the principles and concepts of the present invention and generally designated by the reference numeral 10 will be described.

The present invention, the new and improved fluid deliver system, is comprised of a plurality of components. Such components in their broadest context include a pair of bags, lumens, filters, and a drip control assembly. Such components are individually configured and correlated with respect to each other so as to attain the desired objective.

More specifically, it will be noted that the system 10 of the present invention includes a pair of bags 12 each constructed from a formidable material. Each bag has an eyelet 14 formed on a top edge thereof for allowing the coupling thereof to a horizontally oriented support. Such coupling is afforded preferably via a ring 16. An opening 18 is formed in a bottom edge of each of the bags. The bags include a first bag 20 for containing a first liquid and a second bag 22 for containing a second liquid. The fluids preferably consist of blood and saline mixture, respectfully.

Figure 2:
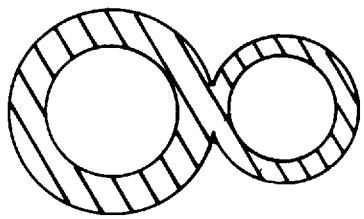
FIG. 2 is a cross-sectional view of the lumens taken along line 2—2 shown in FIG. 1.

As shown in FIG. 1, a pair of elongated lumens 24 are provided each with a top open end and a bottom open end. The lumens consist of a first lumen with a first diameter and a second lumen with a second diameter which is larger than the first diameter. See FIG. 2. The bottom open end of each lumen is fused together to form a single exit conduit 26. It should be noted that the lumens are connected in parallel relationship along lower halves only.

Further included is a pair of filters 28 each connected between the opening of a corresponding bag and the top open end of a corresponding lumen. Such filters are included for filtering the fluid which flows therethrough to the lumens.

As best shown in FIGS. 1 & 3, a pair of cinches 30 are included. Such cinches are situated on each of the lumens adjacent the top open ends thereof. Each cinch is formed of a small rectangular plate with a generally triangular shaped cut out 32 formed therein. Note FIG. 3. As such, a lumen may be situated within each cut out such that the plate may be slid laterally in perpendicular relationship with the plate to selectively preclude the flow of fluid therethrough.

With specific reference to FIGS. 4–6, a drip control assembly 34 includes a rear extent 35 with a rectangular configuration having a bottom face, a rear face, a front face, and a pair of side faces defining an open top face and an interior space. The interior space is defined by a bottom incline 36 and a pair of vertical side walls. The rear wall has an aperture 38 situated adjacent the bottom face for allowing the passage of the lumens therethrough such that the lumens reside along the bottom incline of the interior space. As shown in FIG. 5, the side walls of the assembly have a pair of horizontally situated grooves 40 formed therein adjacent the top face. The drip control assembly further includes a cylindrical roller 42 with a pair of pins 44 integrally formed coaxially on end faces thereof. Such pins are adapted for being slidably situated within the grooves such that the outflow of the fluid from the exit conduit of the lumens may be controlled. Such is accomplished by the roller pinching the lumens against the bottom incline. As shown in FIGS. 1 & 4, the top open end of the rear extent may be equipped with a strip 45 under which an annular groove of the roller resides. As such, the portion of the roller which resides exterior the housing may be translated within a pair of slots defined by the strip 45. It should be noted the roller may consist of one integral roller or, in an alternate embodiment, comprise of two separate rollers by separating the roller along the groove thereof beneath the strip 45. In such embodiment, it should be noted that an additional groove would be required in the strip 45. By equipping the drip control assembly with a pair of rollers, the rate of flow through the lumens is controlled separately.

The drip control assembly further has a front extent 46 with a cylindrical, configuration. Such front extent includes a first end integrally formed with the front face of the rear extent. The bottom open end of the of the lumens is situated coincident with a second end of the front extent of the drip control assembly. The front extent further has a radially extending annular flange 48 formed coincidently with the second end thereof. See FIG. 6. An adapter tube 50 is integrally coupled to the second end of the front extent in communication with the exit conduit of the lumens for allowing fluid to pass therethrough. It should be noted that the adapter tube has a threaded detent 52 formed therein for allowing the attachment of dispensing mechanisms thereto. A chamber 53 is included within the front extent of the drip control mechanism as shown in FIG. 5. The chamber is situated between and in communication with the exit conduit of the lumens and the adapter tube. As shown in FIG. 5, the chamber is preferably equipped with tapered walls.

Finally, an emergency tube 54 is provided with a first end situated within the front extent of the drip control assembly in communication with the lumens. A second end resides exterior the housing. Such tube is ideally equipped with a one-way valve for only allowing fluid to be entered within the lumens and thereafter to the patient.

The present invention allows the unique manual control of a mixture of fluids being transfused to a patient. The cinches may be manipulated to control the respective amount of each fluid that is administered and the drip control assembly may be utilized to control the rate of flow of the combined fluid.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved fluid deliver system comprising, in combination:

a pair of bags each constructed from a formidable material, each bag having an eyelet formed on a top edge thereof for allowing the coupling thereof to a horizontally oriented support via a ring and further having an opening formed in a bottom edge thereof, the bags including a first bag for containing a first liquid and a second bag for containing a second liquid;

a pair of elongated lumens each with a top open end and a bottom open end, the lumens including a first lumen having a first diameter and a second lumen having a second diameter which is larger than the first diameter, wherein the bottom open end of each lumen is fused together to form a single exit conduit and further the lumens are connected in parallel relationship along lower halves thereof;

a pair of filters each connected between the opening of a corresponding bag and the top open end of a corresponding lumen for filtering the fluid which flows therethrough to the lumens;

a pair of cinches situated on each of the lumens adjacent the top open ends thereof, each cinch formed of a small rectangular plate with a generally triangular shaped cut out formed therein, whereby a lumen may be situated within each cut out such that the plate may be slid laterally to selectively preclude the flow of fluid therethrough;

a drip control assembly including a rear extent with a rectangular configuration having a bottom face, a rear face, a front face, and a pair of side faces defining an open top face and an interior space, the interior space defined by a bottom incline and a pair of vertical side walls, the rear wall having an aperture situated adjacent the bottom face for allowing the passage of the lumens therethrough such that the lumens reside along the bottom incline of the interior space, the side walls of the assembly having a pair of horizontally situated grooves formed therein along the top face, the drip control assembly further including a cylindrical roller with a pair of pins integrally formed coaxially on end faces thereof for being slidably situated within the grooves such that the outflow of the fluid from the exit conduit of the lumens may be controlled, the drip control assembly further having a front extent with a cylindrical configuration having a first end integrally formed with the front face of the rear extent such that the bottom open end of the of the lumens is situated coincident with a second end of the front extent of the drip control assembly, the front extent further having an annular flange formed coincidently with the second end thereof and an adapter tube integrally coupled to the second end in communication with the exit conduit of the lumens for allowing fluid to pass therethrough, the adapter tube having a threaded detent formed therein for allowing the attachment of dispensing mechanisms thereto; and an emergency tube with a first end situated within the front extent of the drip control assembly in communication with the lumens.

2. A fluid deliver system comprising:

a pair of bags having an opening formed in a bottom edge thereof, the bags including a first bag for containing a first liquid and a second bag for containing a second liquid;

a pair of elongated lumens each with a top open end and a bottom open end, each top open end of the lumens connected in communication with the openings of a corresponding bag, the bottom ends in communication with each other to form an exit conduit and communicable with a dispensable apparatus for inserting into an arm of a patient; and a drip control means including a roller connected to the lumens for manually controlling the amount of the first fluid and second fluid which exits the lumens and enters a patient;

wherein the drip control means further includes a rear extent with a rectangular configuration having a bottom face, a rear face, a front face, and a pair of side faces defining an open top face and an interior space, the interior space defined by a bottom incline and a pair of vertical side walls, the rear wall having an aperture situated adjacent the bottom face for allowing the passage of the lumens therethrough such that the lumens reside along the bottom incline of the interior space, the side walls of the assembly having a pair of horizontally situated grooves formed therein alone the top face, the roller having a pair of pins integrally formed coaxially on end faces thereof for being slidably situated within the grooves such that the outflow of the fluid from the exit conduit of the lumens may be controlled, the drip control assembly further having a front extent with a cylindrical configuration having a first end integrally formed with the front face of the rear extent such that the bottom open end of the of the lumens is situated coincident with a second end of the front extent of the drip control assembly, the front extent further having an annular flange formed coincidently with the second end thereof and an adapter tube integrally coupled to the second end in communication with the exit conduit of the lumens for allowing fluid to pass therethrough, the adapter tube having a threaded detent formed therein for allowing the attachment of dispensing mechanisms thereto.

3. A fluid deliver system as set forth in claim 2 and further including an emergency tube with a first end situated within the drip control means in communication with the lumens.

4. A fluid deliver system as set forth in claim 2 wherein the lumens include a first lumen having a first diameter and a second lumen having a second diameter which is larger than the first diameter.

5. A fluid deliver system as set forth in claim 2 and further including a pair of filters each connected between the opening of a corresponding bag and the top open end of a corresponding lumen for filtering the fluid which flows therethrough to the lumens.

6. A fluid deliver system as set forth in claim 2 and further including a pair of cinches situated on each of the lumens adjacent the top open ends thereof, each cinch formed of a small rectangular plate with a generally triangular shaped cut out formed therein, whereby a lumen may be situated within each cut out such that the plate may be slid laterally to selectively preclude the flow of fluid therethrough.

7. A fluid deliver system as set forth in claim 2 wherein the drip control means allows for independently controlling the amount of the first fluid and second fluid which exits the lumens and enters a patients.

\* \* \* \* \*